(12) United States Patent
Kikuchi

(10) Patent No.: US 10,441,132 B2
(45) Date of Patent: Oct. 15, 2019

(54) METHOD OF CONTROLLING ENDOSCOPES, AND ENDOSCOPE SYSTEM

(71) Applicant: OLYMPUS CORPORATION, Tokyo (JP)

(72) Inventor: Satoru Kikuchi, Tokyo (JP)

(73) Assignee: Olympus Corporation, Tokyo (JP)

( * ) Notice: Subject to any disclaimer, the term of this patent is extended or adjusted under 35 U.S.C. 154(b) by 544 days.

(21) Appl. No.: 15/172,286

(22) Filed: Jun. 3, 2016

(65) Prior Publication Data
US 2016/0353969 A1     Dec. 8, 2016

Related U.S. Application Data

(63) Continuation of application No. PCT/JP2014/080307, filed on Nov. 17, 2014.

(30) Foreign Application Priority Data

Dec. 5, 2013  (JP) ................................ 2013-252001

(51) Int. Cl.
*A61B 1/00* (2006.01)
*A61B 1/005* (2006.01)
(Continued)

(52) U.S. Cl.
CPC ........ *A61B 1/00006* (2013.01); *A61B 1/0014* (2013.01); *A61B 1/0051* (2013.01);
(Continued)

(58) Field of Classification Search
CPC ............ A61B 1/00006; A61B 1/00057; A61B 1/0014; A61B 1/00154; A61B 1/0051;
(Continued)

(56) References Cited

U.S. PATENT DOCUMENTS 5,368,015 A  * 11/1994  Wilk .................. A61B 1/00147
                                                    600/104
5,609,563 A    3/1997  Suzuki et al.
(Continued)

FOREIGN PATENT DOCUMENTS

EP    1 854 420 A1    11/2007
JP    H05-228096 A     9/1993
(Continued)

OTHER PUBLICATIONS

Extended Supplementary European Search Report dated Jul. 3, 2017 in European Patent Application No. 14 86 6974.0.
(Continued)

*Primary Examiner* — Timothy J Neal
*Assistant Examiner* — Jae Woo
(74) *Attorney, Agent, or Firm* — Scully Scott Murphy & Presser, P.C.

(57) ABSTRACT

A method of controlling an endoscope includes,
inserting an insert part having an imaging unit at a distal end through the body;
making an imaging direction of the imaging unit variable by bending of a bending part,
wherein the bending part is included in the insert part;
detecting an amount of insertion of the insert part through the body; and
determining whether the bending part is to be bent or not on the basis of operation of a direction input part depending on the amount of insertion.

4 Claims, 17 Drawing Sheets

(51) Int. Cl.
    *A61B 34/20*     (2016.01)
    *A61B 1/045*     (2006.01)
    *A61B 5/06*     (2006.01)
    *G02B 23/24*     (2006.01)
    *A61B 17/34*     (2006.01)
    *A61B 17/00*     (2006.01)
    *A61B 90/00*     (2016.01)
    *A61B 1/05*     (2006.01)

(52) U.S. Cl.
    CPC ........ *A61B 1/0055* (2013.01); *A61B 1/00057* (2013.01); *A61B 1/00154* (2013.01); *A61B 1/045* (2013.01); *A61B 5/06* (2013.01); *A61B 34/20* (2016.02); *G02B 23/2476* (2013.01); *A61B 1/00071* (2013.01); *A61B 1/05* (2013.01); *A61B 17/3421* (2013.01); *A61B 2017/00477* (2013.01); *A61B 2034/2059* (2016.02); *A61B 2090/062* (2016.02); *A61B 2090/0811* (2016.02); *G02B 23/24* (2013.01)

(58) Field of Classification Search
    CPC . A61B 1/0055; A61B 1/045; A61B 2034/301; A61B 2034/302
    See application file for complete search history.

(56) References Cited

U.S. PATENT DOCUMENTS

| | | | | |
|---|---|---|---|---|
| 7,087,013 B2* | 8/2006 | Belson | | A61B 1/0053 600/145 |
| 7,090,683 B2* | 8/2006 | Brock | | A61B 17/0469 606/1 |
| 7,371,210 B2* | 5/2008 | Brock | | A61B 17/0469 600/114 |
| 8,858,424 B2* | 10/2014 | Hasegawa | | A61B 1/0051 600/106 |
| 9,895,143 B2* | 2/2018 | Inoue | | A61B 1/0052 |
| 2007/0150155 A1* | 6/2007 | Kawai | | A61B 1/00059 701/72 |
| 2007/0265502 A1* | 11/2007 | Minosawa | | A61B 1/00177 600/173 |
| 2008/0086029 A1* | 4/2008 | Uchiyama | | A61B 1/01 600/114 |
| 2009/0105726 A1* | 4/2009 | Sugiyama | | A61B 18/1492 606/130 |
| 2010/0262162 A1* | 10/2010 | Omori | | A61B 1/00149 606/130 |
| 2016/0213364 A1* | 7/2016 | Inoue | | A61B 1/0052 |
| 2016/0302653 A1* | 10/2016 | Inoue | | G01C 3/08 |

FOREIGN PATENT DOCUMENTS

| | | | |
|---|---|---|---|
| JP | 2003-070717 A | 3/2003 | |
| JP | 2003-337289 A | 11/2003 | |
| JP | 2006-055349 A | 3/2006 | |
| JP | 2008-093029 A | 4/2008 | |
| JP | 4398479 B2 | 1/2010 | |
| JP | 4754740 B2 | 8/2011 | |
| JP | 2015024026 A * | 2/2015 | ........... A61B 1/0052 |

OTHER PUBLICATIONS

International Search Report dated Jan. 13, 2015 issued in PCT/JP2014/080307.

* cited by examiner

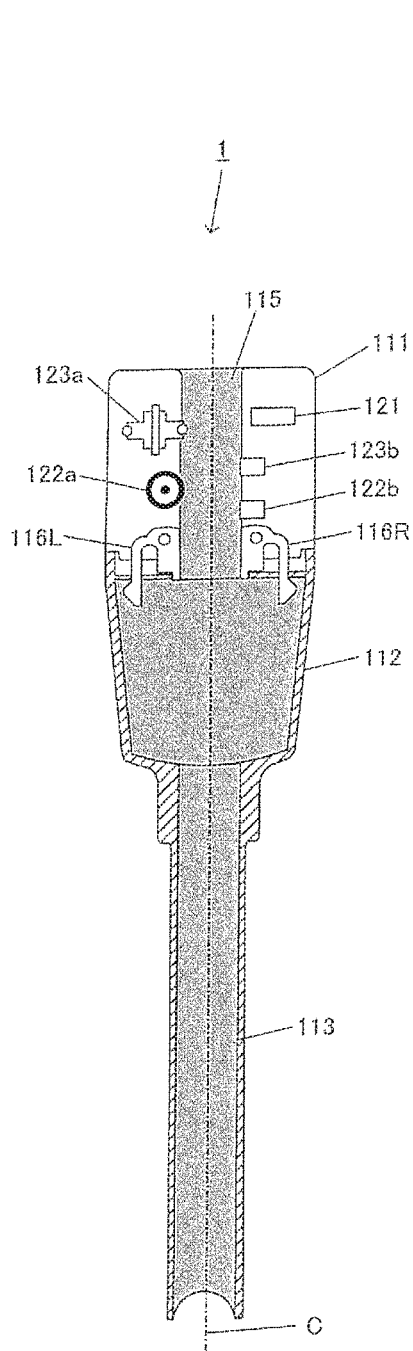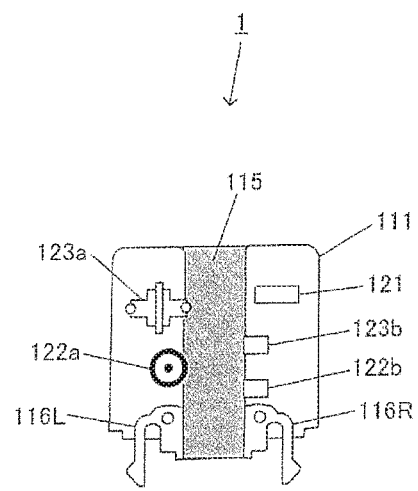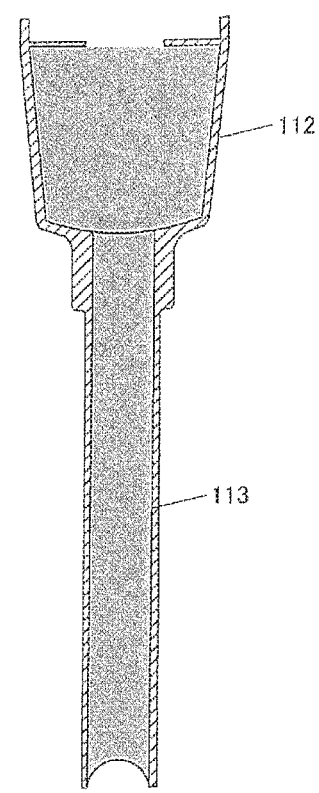
FIG.6A    FIG.6B

METHOD OF CONTROLLING ENDOSCOPES, AND ENDOSCOPE SYSTEM

CROSS-REFERENCE TO RELATED APPLICATIONS

This application is a continuation claiming priority on the basis of Japan Patent Application No. 2013-252001 applied in Japan on Dec. 5, 2013 and based on PCT/JP2014/080307 filed on Nov. 17, 2014. The contents of both the PCT application and the Japan Application are incorporated herein by reference.

BACKGROUND OF THE INVENTION AND RELATED ART STATEMENT

The present invention relates to a method of controlling an endoscope that is inserted through the body of a patient for surgical operation to view the interior of the patient's body as well as an endoscope system.

Currently, a trocar is inserted from the body surface of a patient through the interior of the body to inject gas into the body (pneumoperitoneum) and various medical instruments are inserted through the trocar to carry out laparoscopic surgery for various treatments and medical examinations in the interior of the body. Although this laparoscopic surgery is less invasive on patients because of making do with a limited incision in the body surface of the patient, much is still left to be desired in terms of the visibility of an endoscope and the operability of the endoscope and medical instruments because there is the need for performing surgery while observing the interior of the patient's body.

Japanese Patent No. 4754740 discloses an endoscope apparatus used for laparoscopic surgery wherein a hard part is divided into a distal end part and a proximal end part, and a bendable joint part and a fixing means for keeping the bending state of the joint part are provided between the distal end part and the proximal end part. With such an endoscope apparatus, it is possible to adjust the angle of bending of the joint part to any desired angle between the distal end part and the proximal end part thereby holding the joint part adjusted by the fixing means at any desired angle.

SUMMARY OF INVENTION

In one embodiment of a method of controlling an endoscope according to the invention, the method of controlling an endoscope includes, inserting an insert part having an imaging unit at a distal end through the body;

making an imaging direction of the imaging unit variable by bending of a bending part, wherein the bending part is included in the insert part;

detecting an amount of insertion of the insert part through the body; and determining whether the bending part is to be bent or not on the basis of operation of a direction input part depending on the amount of insertion.

In one embodiment of an endoscope system according to the invention, the endoscope system includes an insert part and a control unit, wherein:

the insert part includes an imaging unit provided at a distal end and a bending part capable of bending movement to make an imaging direction of the imaging unit variable, and can be inserted through the body, the control unit is capable of implementing amount-of-insertion control processing and bending part control processing, the amount-of-insertion detection processing detects an amount of insertion of the insert part through the body, and the bending part control processing is implemented on the basis of an amount of insertion detected by the amount-of-insertion detection processing to determine whether the bending part is to be bent or not on the basis of operation of a direction input part.

BRIEF DESCRIPTION OF DRAWINGS

FIGS. 6A and 6B are illustrative of the internal construction of the trocar according to one embodiment of the invention.

DESCRIPTION OF EMBODIMENTS

Figure 1:
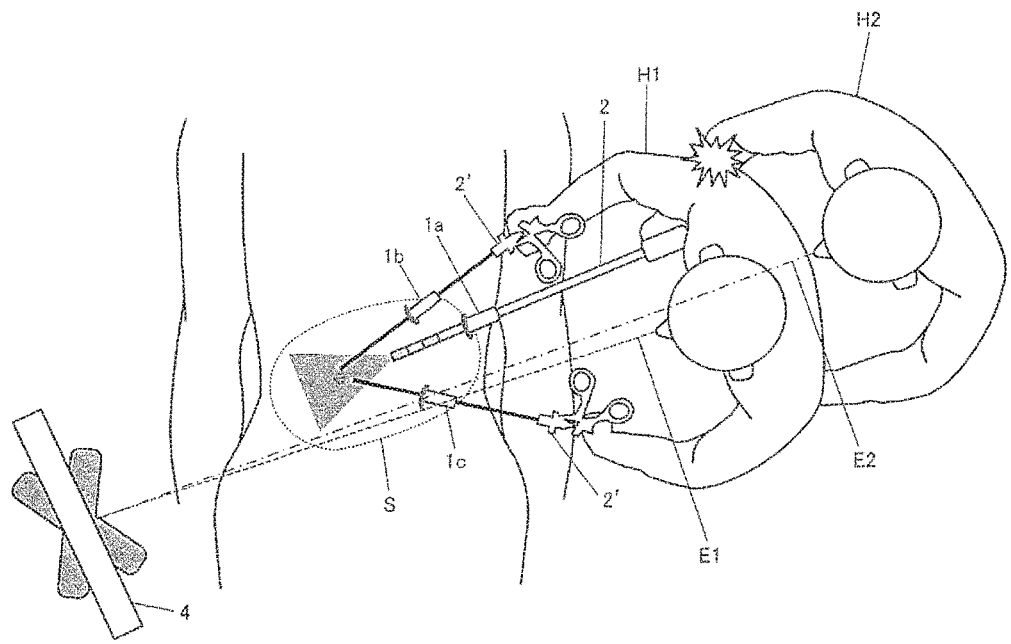
FIG. 1 is illustrative of how to carry out conventional laparoscopic surgery using an endoscope.

FIG. 1 is illustrative of how to carry out conventional laparoscopic surgery using various medical instruments. In laparoscopic surgery, there are plural holes cut open in the abdomen or the like of a patient to inject gas in the abdominal cavity for formation of a space in the patient's body (pneumoperitoneum). Then, various medical instruments such as an endoscope 2, forceps 2' and (electric) scalpels are inserted through the space in the patient's body for viewing and treatment of an affected site while viewing images taken through the endoscope 2. This laparoscopic surgery is less invasive of patients because of requiring less incision area.

In laparoscopic surgery, tubes called trocars (channels) 1a to 1c are inserted in openings cut open in the patient's body wall, and various medical instruments are inserted through the patient via the trocars 1a to 1c. the endoscope 2 is being inserted through the trocar 1a while the forceps 2' are being inserted through the trocars 1b and 1d. On the distal end of the endoscope 2, there is an imaging unit mounted to show images taken by an imaging unit on a display unit such as a monitor. Usually, the endoscope 2 is manipulated by an assistant H2 called the "scopist", and the site of interest is imaged on the basis of an instruction from a surgeon H1. The forceps 2' are provided at the distal end with a distal end gripper that works as an end effector, and the surgeon H1 manipulates the forceps 2' to open or close or otherwise handle the distal end gripper for surgical operation of an affected site. With laparoscopic surgery, it is thus possible for the surgeon H1 to use the forceps 2' for surgical operation while viewing images taken through the endoscope 2.

FIG. 1 is illustrative of how conventional laparoscopic surgery is carried out by the surgeon H1 and assistant H2. In laparoscope surgery, the assistant H2 as the scopist manipulates the endoscope 2 to show images in the interior of the abdominal space S that are necessary for the surgeon H1 on a monitor 4. When the display screen of the monitor 4 is shared by the surgeon H1 and assistant H2, the surgeon H1 may possibly interfere with (or strike upon) the assistant H2, detracting from the operability of the medical instruments on both sides. In addition, when the direction of surgical operation carried out by the surgeon H1 coincides nearly with the direction of imaging by the assistant H2, it is likely that the direction E2 of the line of sight of the assistant H2 in particular may be blocked off by the surgeon H1 for the reason that the directions E1 and E2 of the lines of sight of the surgeon H1 and assistant H2 with respect to the monitor 4 are much the same. This will in turn detract from the visibility of the assistant H2 with respect to the monitor 4.

Figure 2:
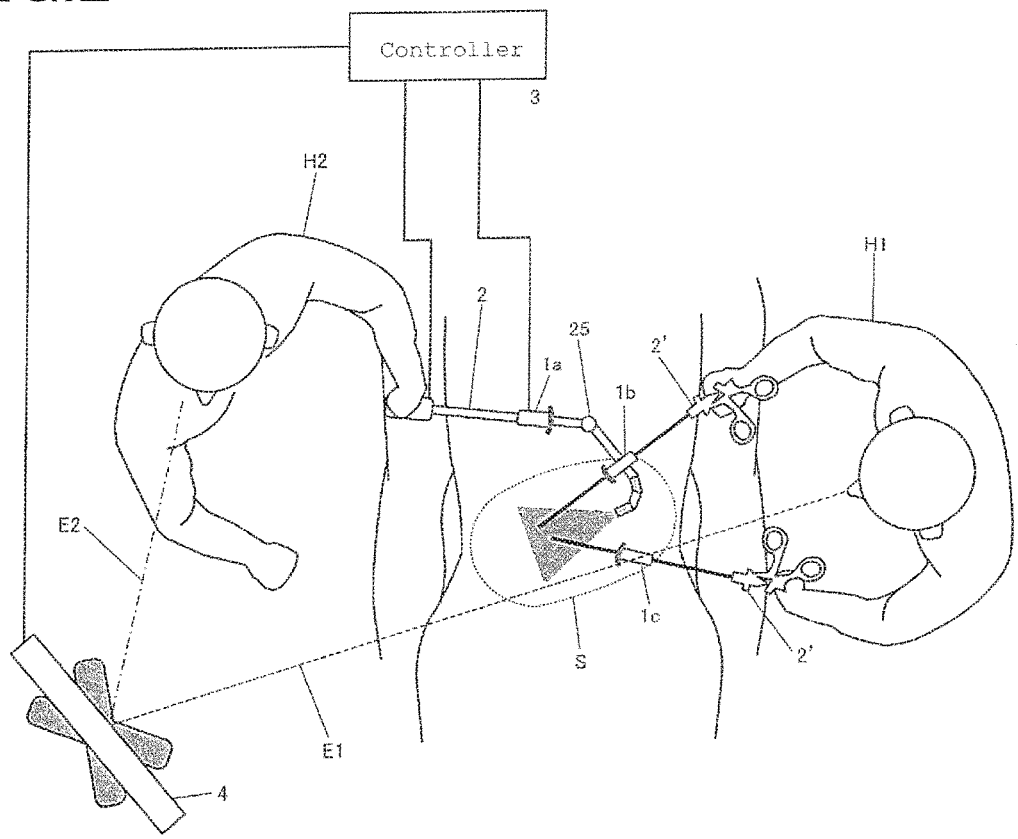
FIG. 2 is illustrative of how to carry out laparoscopic surgery using the endoscope according to one embodiment of the invention.

The endoscope system according to one embodiment of the invention has for its object to make improvements in operability and visibility in such laparoscopic surgery as mentioned above. FIG. 2 is illustrative of how laparoscopic surgery is carried out using the endoscope 2 according to one embodiment of the invention. The endoscope 2 described herein has a feature of having a bending part 25 capable of being bent in the interior of the abdominal space S of a patient. In surgical operation carried out in the interior of the abdominal space S, it is possible for the assistant H2 to bend the bending part 25 mounted on the endoscope 2 in the interior of the abdominal space S. Accordingly, when surgical operation is performed on the same affected site in the interior of the abdominal space S as in FIG. 1, the surgeon H1 and assistant H2 may take up positions where they do not interfere with (or strike upon) each other, as depicted in FIG. 2, resulting in improvements in the operability of the medical instruments by both. When both share the common monitor 4 for viewing images too, there is visibility improved without interference of the direction E1 of the line of sight of the surgeon H1 with the direction E2 of the line of sight of the assistant H2.

Figure 3:
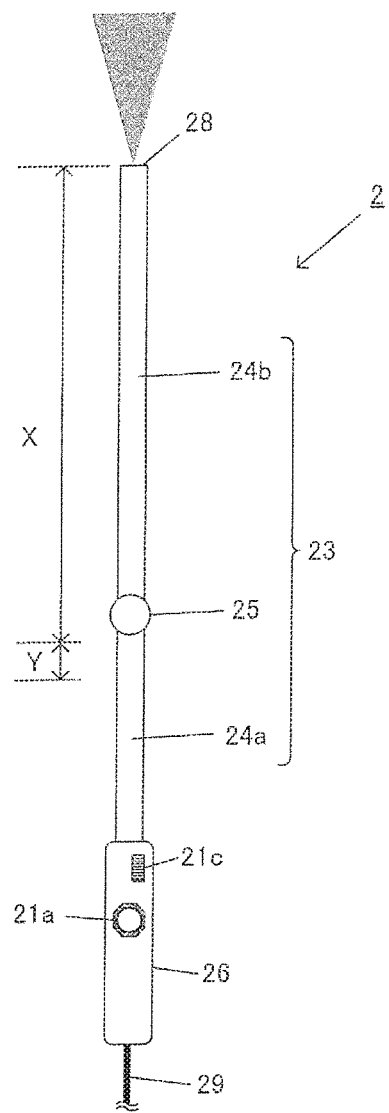
FIG. 3 is illustrative of the construction of the endoscope according to one embodiment (Example 1) of the invention.

FIG. 3 is illustrative in construction of the endoscope 2 according to one embodiment (Example 1) of the invention. The endoscope 2 described herein includes a gripper member 26 grasped by an operator, and an insert part 23. In the embodiment described herein, the insert part 23 to be inserted through the abdominal space of a patient includes a first shaft 24a connected to the gripper member 26, a second shaft 24b provided at the distal end with an imaging unit 28, and a bending part 25 for connecting together the first shaft 24a and second shaft 24b in a bendable manner.

The gripper member 26 is provided with a direction input part 21a and a magnification input part 21c in the form of a combined input unit 21 capable of receiving an input from the operator. A driver 22 (not shown) positioned within the gripper member 26 or the like is driven in accordance with the amount of operation the direction input part 21a for bending movement of the bending part 25 to rotate the second shaft 24b. The gripper member 26 is provided with the magnification input part 21c for designating the magnification of images obtained through the imaging unit 28. The magnification input part 21c may have various forms capable of designating the magnification of the obtained images such as a dial input form or a switch input form capable of designating zooming-in and zooming-out. While the magnification change of images is preferably made by means of optical zooming involving active movement of a lens within the imaging unit 28, it is to be understood that use may also be made of digital zooming for varying magnification by image processing of the obtained images alone or in combination with optical zooming.

The gripper member 26 includes a cable 29 for external output of image signals obtained through the imaging unit 28, the bending state of the bending part 25, and various input signals received at the input unit 21 or input of various signals from a controller 3. Connection of the cable 29 to the controller 3 enables viewing of images by the endoscope 2 and various controls of the endoscope as well.

Figures 4A, 4B, 4C:
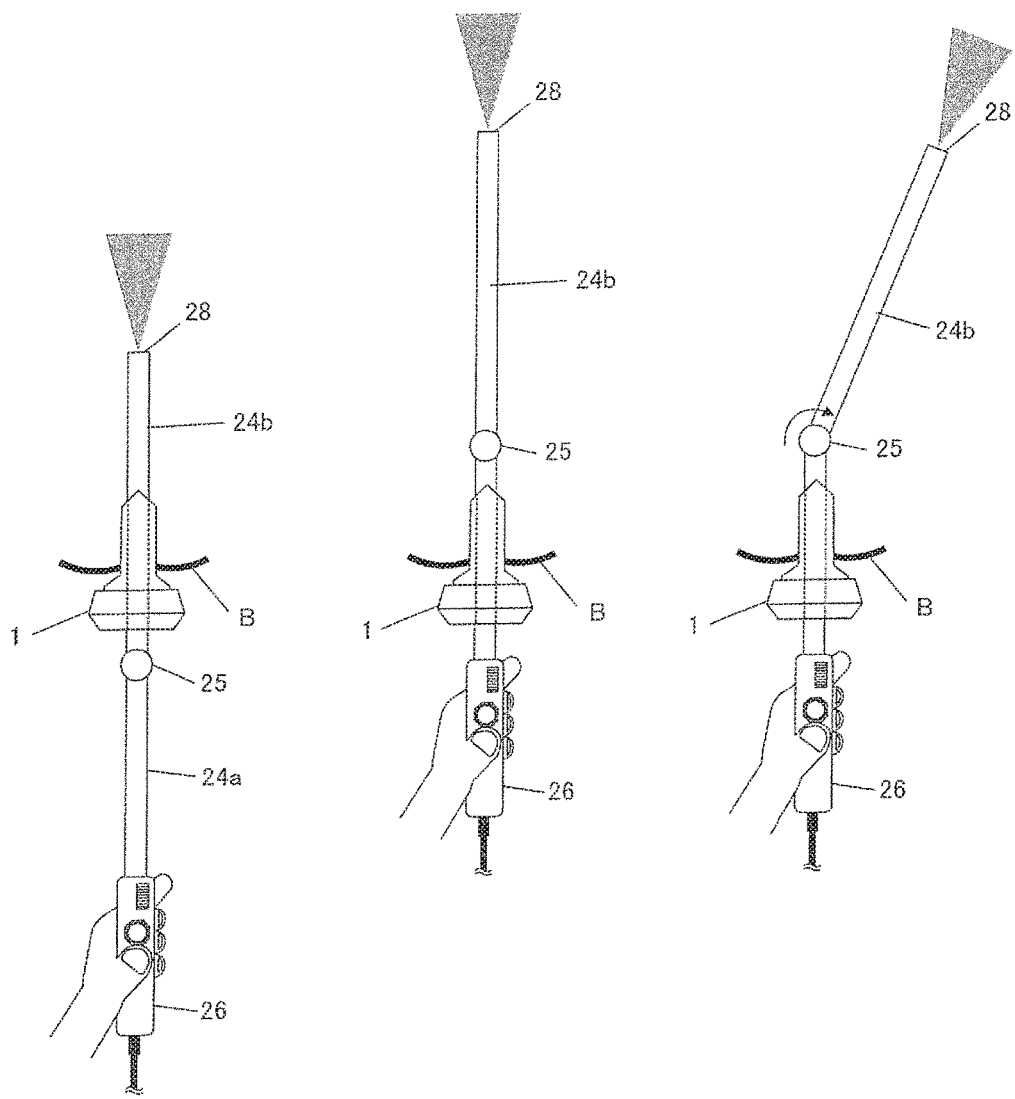
FIG. 4A-4C are illustrative of a control configuration for the endoscope according to one embodiment (Example 1) of the invention.

FIG. 4A-4C is illustrative of how the endoscope 2 explained with reference to FIG. 3 is inserted through the patient's body and how it is controlled. Insertion of the insert part 23 through the patient's body is implemented by way of the trocar 1 located on the patient's body surface B. When the insert part 23 includes the bending part 25 as described herein, the bending part 25 must be placed in an unbent state; that is, the first 24a and second shaft 24b must be kept just straight as depicted in FIG. 4A because the insert part 23 cannot pass through the trocar 1 when the bending part 25 remains bent. The insert part 23 is inserted in such a state until the bending part 25 goes through the trocar 1; that is, while the bending part 25 remains in the patient's abdominal space as depicted in FIG. 4B, the direction input part 21a is operated to bend the bending part 25 such that the imaging unit 28 turns in any desired direction.

With the endoscope 2 including the bending part 25 as described herein, it is thus possible to improve on operability and visibility in the case of laparoscopic surgery in which personnel take part as explained with reference to FIG. 2. However, the bending part 25 does not normally bend unless it goes through the trocar 1 or, alternatively, forced bending of the bending part 25 within the trocar 1 will possibly lead to a breakage or failure of the endoscope 2 or trocar 1.

The endoscope system according to the invention has for its one object to improve on the operability of the endoscope 2 including the bending part 25 in the insert part 23. In the endoscope system according to the embodiment of the invention described herein, therefore, the amount of insertion of the insert part 23 through the body is detected to determine whether the bending part 25 is to be bent or not on the basis of the detected amount of insertion. In the embodiment described herein, the positional relation of the bending part 25 and trocar 1 is determined on the basis of the amount of insertion to enable bending movement of the bending part 25 by a direction input part 21a in the case where the bending part 25 remains in the abdominal space, and disable bending movement of the bending part 25 by the direction input part 21a in the case where the bending part 25 remains within the trocar 1, thereby making sure bending movement of the bending part 25 within the abdominal space and holding back interference between the endoscope 2 and the trocar 1 due to malfunctions or the like. Note here that the amount of insertion of the insert part 23 through the body may be determined not only by detection of the positional relation of the trocar 1 to the insert part 23 but also by various forms including a specific form of detecting the positional relation of the insert part 23 to the patient's body surface by means of various sensors inclusive of a camera.

Figure 7:
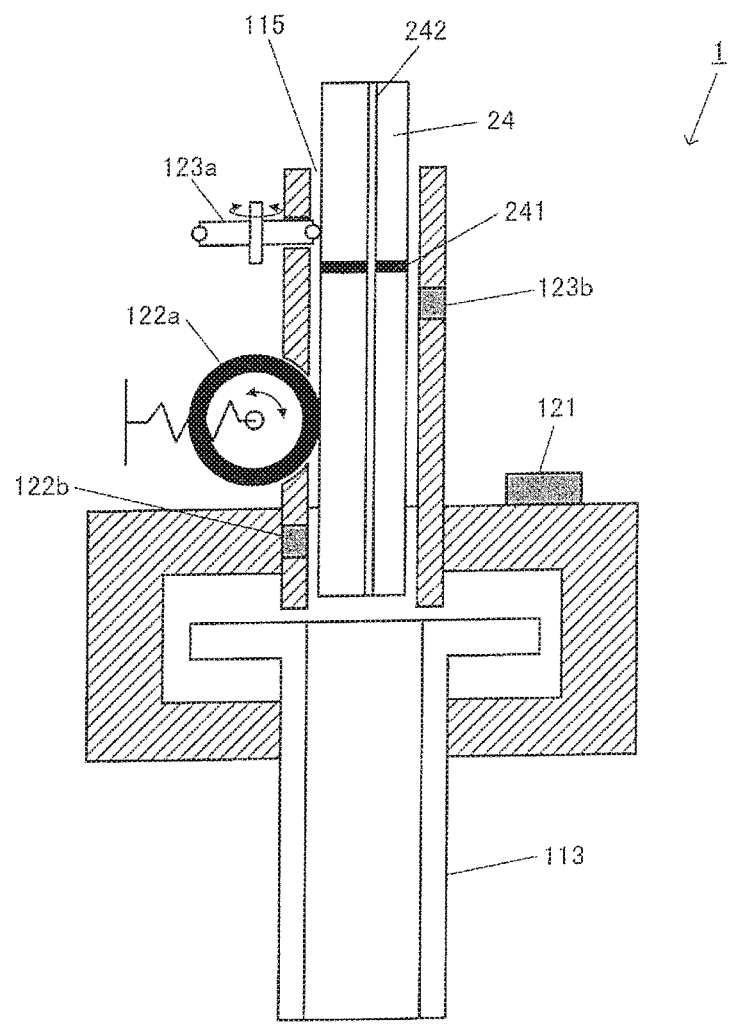
FIG. 7 is illustrative in schematic of the internal construction of the trocar sensor according to one embodiment of the invention.

While there may be some possible forms for detection of the amount of insertion of the insert part 23, it is here assumed that states of the medical instruments such as the endoscope 2 including the amount of insertion (determinable on the basis of the amount of advanceable/retractable movement) detected by means of various sensors mounted on the trocar 1 are used. For this reason, the construction of the trocar 1 including various sensors is illustrated in FIGS. 5, 6 and 7.

Figure 5:
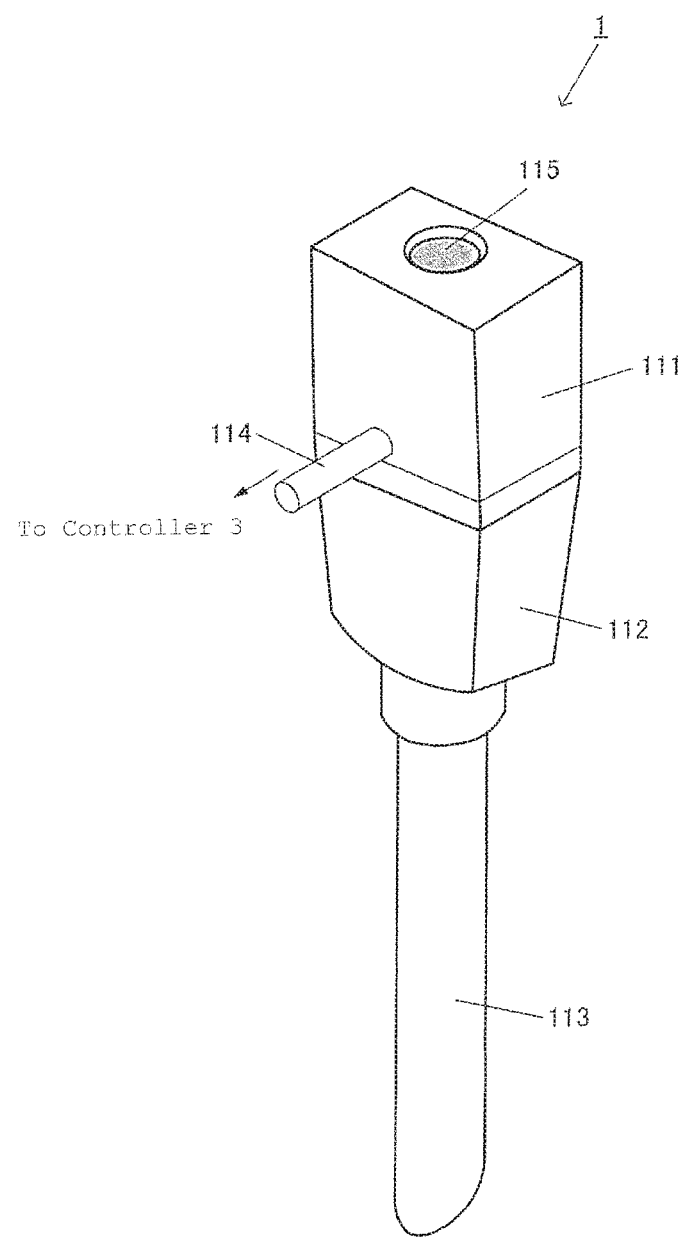
FIG. 5 is illustrative of the external appearance of the trocar according to one embodiment of the invention.

FIG. 5 is illustrative of the external appearance of the trocar 1 that may be used with the medical system according to one embodiment of the invention. The trocar 1 described herein includes an upper housing 111, a lower housing 112 and a cylindrical tube 113. The upper housing 111 is provided with an insertion path 115 for insertion of various medical instruments. The cylindrical tube 113 is inserted through the patient's body. A medical instrument inserted from the insertion path 115 goes through the lower housing 112 and cylindrical tube 113, and is inserted from the lower end of the cylindrical tube 113 into the patient's body for viewing the interior of the patient's body or surgical treatments in the patient's body.

Within the upper housing 111 there are various sensors provided for detection of the states of the medical instrument inserted from the insertion path 115. Signals produced out of various sensors are sent out to the controller 3 by way of a cable 114. Note here that the cable 114 has another function of feeding power supply to various sensors. While communication between the sensors and the controller 3 may be of such a wired type, it is to be understood that use of wireless communication and battery-activated driving may lead to elimination of the cable 114 from the trocar 1.

FIGS. 6A and 6b are a sectional view of the internal construction of the trocar 1 according to one embodiment of the invention. While the upper housing 111 is shown to have the insertion path 115 as explained with reference to FIG. 5, it is to be noted that a brown part from the insertion path 115 down to the lower end of the cylindrical tube 113 is a communicating section through which various medical instruments are to be inserted. The upper 111 and lower housing 112 may be coupled to or decoupled from each other by means of coupler members 116R and 116L, each in a clip form. During use of the trocar 1, the upper 111 and lower housing 112 are coupled together, and for cleaning or other purposes, the upper housing 111 may be removed out from the lower housing 112 as depicted in FIG. 6B. This facilitates cleaning, disinfection or replacement of the cylindrical tube 113 as well as maintenance of the upper housing 111 including various sensors. Note here that the trocar 1 may be designed as a single housing in which the upper housing 111 is integral with the lower housing 112.

In the trocar 1 according to the embodiment described herein, the upper housing 111 includes various sensors (for instance, a trocar sensor 12) inside. In the embodiment described herein, the trocar sensor 12 includes a tilt angle detection sensor 121, an amount-of-advanceable/retractable-movement detection sensor 122, and an amount-of-rotation detection sensor 123. The tilt angle detection sensor 121 is provided for detecting the tilt angle of the trocar 1, that is, in which direction the trocar 1 turns with respect to a reference coordinate system. The reference coordinate system here is the one that is defined relative to a fixed object such as a patient or the ground, and various sensors inclusive of an acceleration sensor may be used for the tilt angle detection sensor 121. The acceleration sensor may detect an acceleration applied thereon to detect in which direction the trocar 1 turns, that is, the tilt angle of the trocar 1 with respect to the reference coordinate system.

The amount-of-advanceable/retractable-movement detection sensor 122 is provided for detection of the amount-of-advanceable/retractable-movement of a medical instrument inserted through the trocar 1 in its insertion direction (in the vertical direction in FIGS. 6A and 6B). As already explained with reference to FIG. 1, a surgeon such as a physician inserts or withdraw a medical instrument through the trocar 1 to operate and move the medical instrument within the patient's body to an unerring position. With the amount-of-advanceable/retractable-movement detection sensor 122, it is possible to detect the insertion position of the medical instrument relative to the trocar 1 in the form of the amount of advanceable/retractable movement. FIG. 6A shows the center axis C of the trocar 1 in the insertion direction by a dashed line. The amount-of-advanceable/retractable-movement detection sensor 122 detects the amount of movement parallel with that center axis C in the form of the amount of advanceable/retractable movement. In the embodiment described herein, the amount-of-advanceable/retractable-movement detection sensor 122 is made up of a combined amount-of-advanceable/retractable-movement detection roller 122a and photosensor 122b.

The amount-of-rotation detection sensor 123 is provided for detection of the amount of rotation of a medical instrument that rotates in association with operation as by a surgeon. By rotational operation about the center axis C of a medical instrument inserted through the insertion path 115, it is possible to change the direction or orientation of the end effector mounted at the distal end of the medical instrument within the patient's body. The amount-of-rotation detection sensor 123 detects this amount of rotation so that in which direction the end effector of the medical instrument turns can be detected. The amount-of-rotation detection sensor 123 is made up of a combined amount-of-rotation detection roller 123a and photosensor 123b.

While the internal construction of the trocar 1 has been explained, it is to be understood that the trocar sensor 12 disposed within the trocar 1 sends a detection signal out to the controller 3 by way of a communication unit 13 not shown in FIGS. 6A and 6B. Actuation of the trocar sensor 12 in the embodiment described herein is now explained with reference to FIG. 7 that is a schematic view of the construction of the trocar sensor 12. FIG. 7 is illustrative in schematic of the construction of the trocar sensor 12 disposed within the trocar 1 of FIGS. 6A and 6B, showing that the first shaft 24 of the medical instrument is being inserted through the trocar 1. Note here that FIG. 7 does not show an end effector and so on attached to the distal end of the medical instrument.

There is some margin given to the diameter of the insertion path 115 for the trocar 1 in such a way as to receive the insertion part of the medical instrument such as the first shaft 24. The trocar 1 will be fixed near to the patient's body surface, but it will rotate pivotally with a certain point as reference in association with operation of the medical instrument. The tilt angle detection sensor 121 fixed to the housing of the trocar 1 is capable of detecting pivotal rotation of the trocar 1 to detect the direction of the trocar 1, i.e., the direction of the medical instrument in the reference coordinate system.

In the embodiment described herein, the amount-of-advanceable/retractable-movement detection sensor 122 is made up of a combined amount-of-advanceable/retractable-movement detection roller 122a and photosensor 122b as explained with reference to FIGS. 6A and 6B. The amount-of-advanceable/retractable-movement detection roller 122a has a direction vertical to the plane of FIG. 7 as a rotary axis. This amount-of-advanceable/retractable-movement detection roller 122a is biased by a resilient member like a spring toward the insertion path 115, and comes into contact with the surface of the medical instrument (the first shaft 24) inserted through the insertion path 115 to convert the amount of advanceable/retractable movement of the medical instrument into its amount of rotation. The rotary axis of the amount-of-advanceable/retractable-movement detection roller 122a is provided with an encoder to produce out the amount of rotation of the amount-of-rotation detection roller 122a in the form of the amount of advanceable/retractable movement. In the embodiment described herein, the photosensor 122b facing in the insertion path 115 is provided so as to calibrate the amount of advanceable/retractable movement (set it to the initial value). This photosensor 122b is capable of detecting a position-of-advanceable/retractable-movement detection mark 241 positioned on the medical instrument (the first shaft 24 or the like) to calibrate the amount of advanceable/retractable movement detected by the amount-of-advanceable/retractable-movement detection roller 122a. Upon advanceable/retractable movement of the medical instrument through the insertion path 115, therefore, the amount of advanceable/retractable movement will be calibrated (set to the initial value) each time the position-of-advanceable/retractable-movement detection mark 241 is just past the photosensor 122b, making sure detection of the exact amount of advanceable/retractable movement of the medical instrument relative to the trocar 1.

As already explained with reference to FIGS. 6A and 6B, the amount-of-rotation detection sensor 123 according to the embodiment described herein is made up of a combined amount-of-rotation detection roller 123a and photosensor 123b. The amount-of-rotation detection roller 123a has a rotary axis turning in the vertical direction of FIG. 7. This amount-of-rotation detection roller 123a is biased by a resilient member like a spring toward the insertion path 115, and comes into contact with the surface of the medical instrument (the first shaft 24) inserted through the insertion path 115 to convert the amount of rotation of the medical instrument into the amount of rotation of the amount-of-rotation detection roller 123a. Note here that the contact surface of the amount-of-rotation detection roller 123a is preferably provided with a member (like a bearing) that does not interfere with movement of the medical instrument in the insertion direction. The rotary axis of the amount-of-rotation detection roller 123a is provided with an encoder that produces out the amount of rotation of the amount-of-rotation detection roller 123a in the form of the amount of rotation of the medical instrument. In the embodiment described herein, the photosensor 123b facing in the insertion path 115 is provided so as to calibrate the amount of rotation (set it to the initial value). As with the amount-of-advanceable/retractable-movement detection sensor 122, this photosensor 123b is capable of detecting a position-of-rotation detection mark 242 provided on the medical instrument (the first shaft 24 or the like) to calibrate the amount of rotation detected by the amount-of-rotation detection roller 123a.

While the trocar sensor disposed on the trocar 1 has been explained, it is to be understood that various sensor forms may be used to set up the trocar sensor. In the embodiment described herein, for instance, a mechanical sensor part using rollers is used for detection of the amount of advanceable/retractable movement or rotation, but an optical sensor used with a laser mouth and capable of detecting the amount and direction of surface movement may also be used for detection of the amount of advanceable/retractable movement or rotation. In that case, the amount of advanceable/retractable movement and rotation may be detected with a single optical sensor.

For the medical system according to the embodiment described herein, the amount of insertion of the insert part 23 inserted through the patient's body is required. That amount of insertion is decided on the basis of the amount of advanceable/retractable movement detected by the trocar sensor. In the embodiment described herein, the trocar sensor disposed within the trocar 1 is used for detection of the amount of insertion, but use may also be made of not just the trocar sensor but various sensors located on the side of the endoscope 2 as well. Such various modes as mentioned below may be used for detection of the amount of insertion implemented on the side of the endoscope 2.

(1) The bending part 25 is provided with a stress sensor to detect whether or not there is the bending part 25 remaining within the trocar 1 on the basis of a stress applied to the stress sensor.

(2) An acceleration sensor is provided on the side of the endoscope 2, for instance, on the gripper 26, and the position of the endoscope 2 is detected by tracking the output of the acceleration sensor to decide the positional relation of the endoscope 2 relative to the trocar 1 (the amount of insertion).

(3) Whether or not the bending part 25 remains within the trocar 1 is detected on the basis of an image taken through the imaging unit 28.

Figure 8:
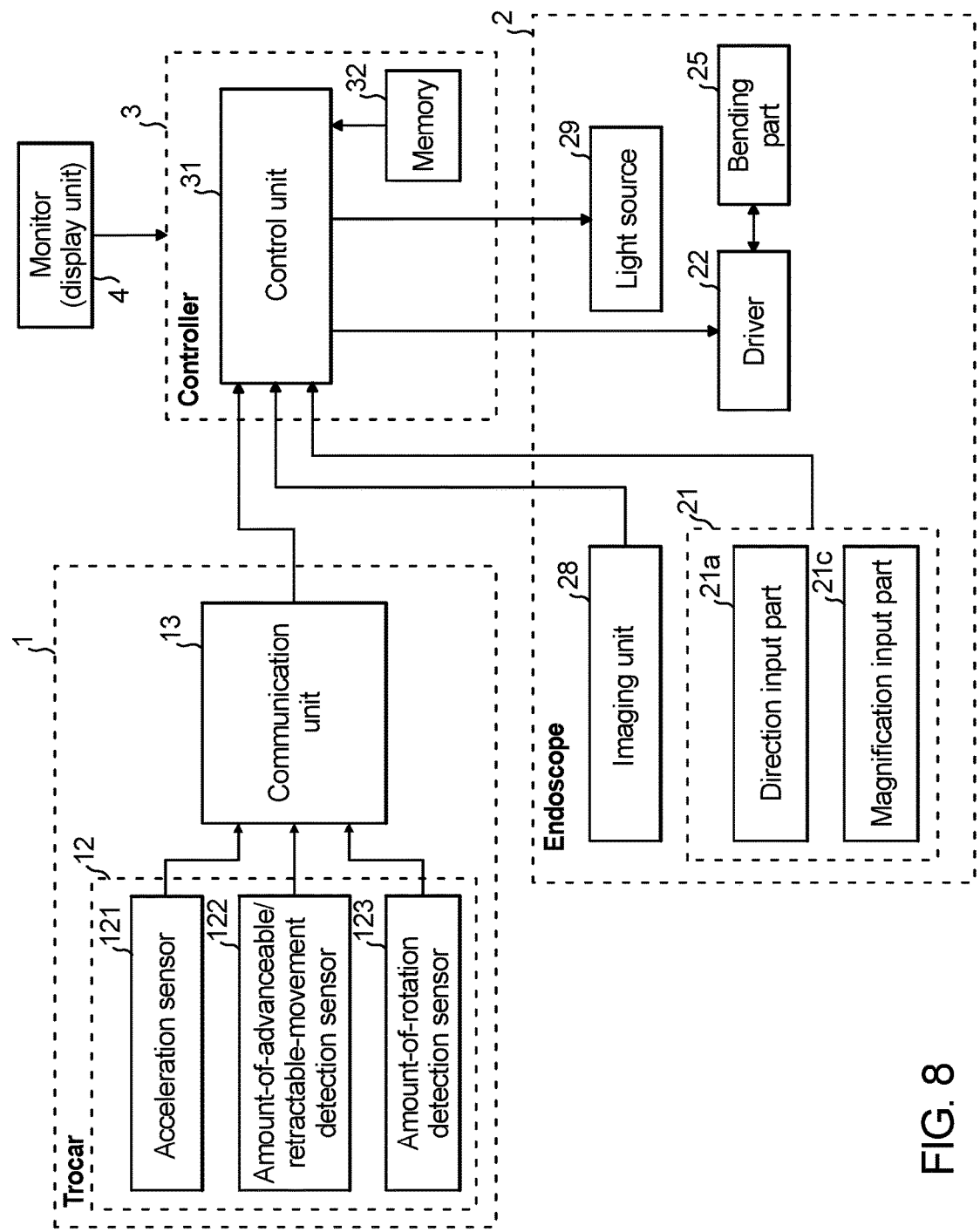
FIG. 8 is illustrative of a control configuration for the endoscope system according to one embodiment (Example 1) of the invention.

FIG. 8 is illustrative of the control configuration for the endoscope system according the embodiment described herein (Example 1). The endoscope system is mainly composed of an endoscope 2 and a controller 3, and further includes external elements such as various sensors mounted on the trocar 1 and a monitor 4 on which images coming from the imaging unit 28, etc. are displayed.

The trocar 1 includes a trocar sensor 12 including a tilt angle detection sensor 121, an amount-of-advanceable/retractable-movement detection sensor 122 and an amount-of-rotation detection sensor 123, a communication unit 13, and a light source 29. The endoscope 2 includes an operation input unit 21 including a direction input part 21a and magnification input part 21c explained with reference to FIG. 3, and a driver 22. The driver 22 is a member such as a motor for rotation of the bending part 25 of the endoscope 2. The driver 22 may be designed such that the bending part 25 is directly rotated by a gear or the like or, alternatively, it is indirectly rotated by a wire or thread. The light source 29 is a lighting means for directing illumination light to the site of interest at the imaging unit 28 mounted to the distal end of the insert part 23. The light source 29 may be located at the imaging unit 28 or, alternatively, it may be provided at the gripper member 26 such that the imaging unit 28 directs illumination light to the site of interest by way of a light guide such as an optical fiber.

The trocar 1 and endoscope 2 are connected to the controller 3. The controller 3 includes a control unit 31 made up of a CPU and so one, and a memory 32 serving as a storage unit. The memory 32 may store various programs running on the medical system, and various signals and data necessary for running the programs.

Figure 9:
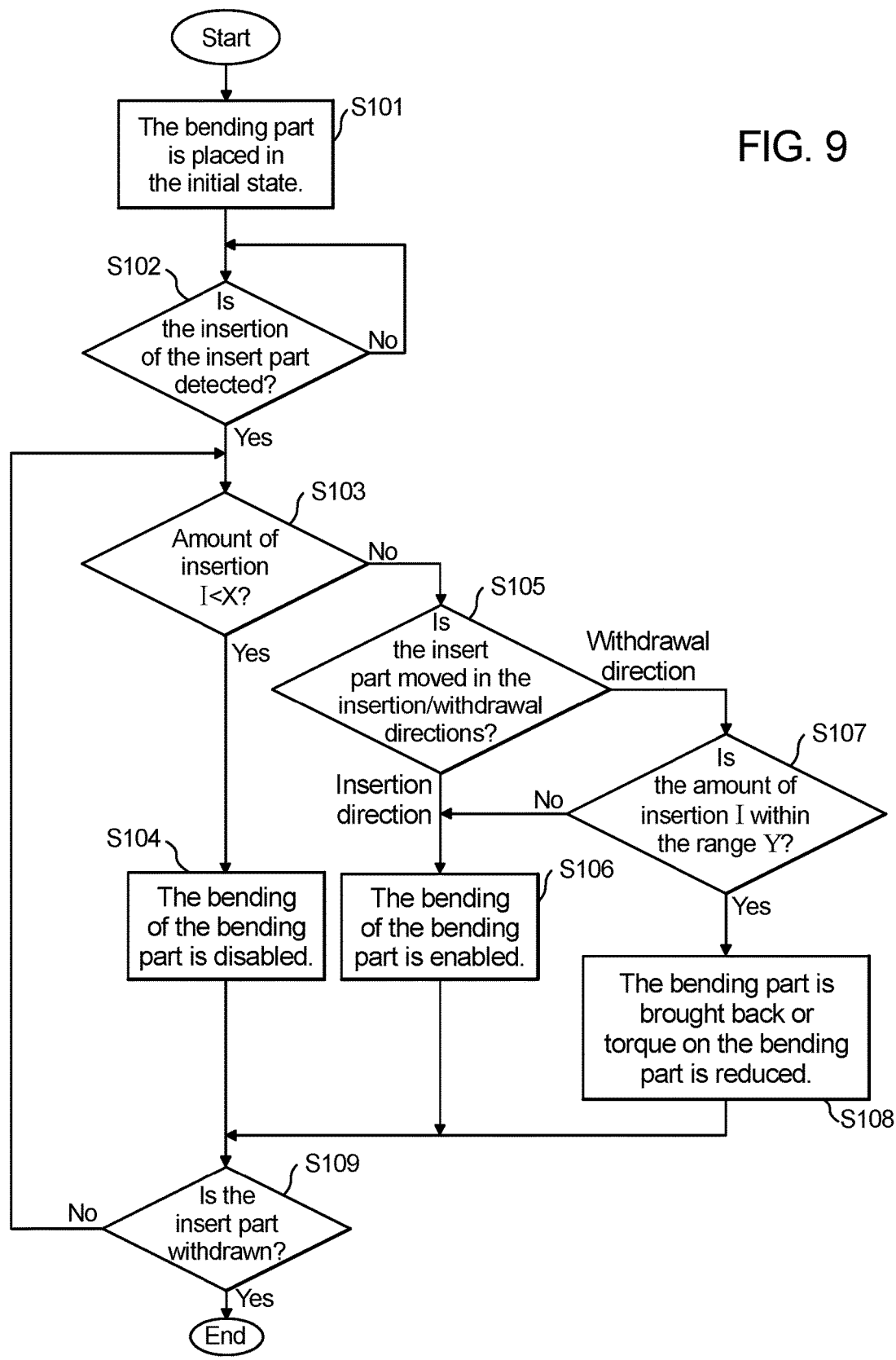
FIG. 9 is a control flow diagram for the endoscope system according to one embodiment (Example 1) of the invention.

How to use such a medical system (endoscope system) is now explained. FIG. 9 is a control flowchart for the endoscope system according to the embodiment described herein. Processing shown in this control flowchart is implemented on the controller 3 during laparoscopic surgery. For an understanding of the construction of the endoscope 2 shown in FIG. 3, the "length" used in that control flowchart is now defined. In the embodiment described herein, the length from the distal end of the second shaft 24b to the first shaft 24a with the bending part 25 in between is defined as X, and the length of a given position on the first shaft is defined as Y.

As the power of the endoscope system is turned on to get processing for the endoscope 2 started, it causes the light source 29 to start illumination and the bending part 25 to be adjusted to its initial state (S101). The "initial state" here is understood to mean processing for keeping the bending part 25 straight enough to pass through the insertion path 115 extending through the trocar 1, as shown in FIG. 4A. In S103 to S109, processing is implemented on the basis of the amount of insertion of the insert part 23 decided on the basis of the amount of advanceable/retractable movement detected by the trocar sensor. As is the case with the already explained length X, the amount of insertion I in the embodiment described herein is defined by a reference position provided by the end position of the imaging unit 28 on the second shaft 24b, the reference position being indicative of a distance of the insert part inserted from the distal end of the trocar 1 through the patient's body. Note here that the amount of insertion I may optionally be determined using other references.

In the embodiment described herein, processing at the time of insertion of the insert part 23 through the patient's body (S105: insertion direction) is different from processing at the time of withdrawal of the insert part 23 out of the patient's body (S105: withdrawal direction). Whether there is insertion or withdrawal may be determined by a change in the amount of advanceable/retractable movement measured by the amount-of-advanceable/retractable-movement detection sensor 122. Processing at the time of insertion is first explained. As the insertion of the insert part 23 is sensed by the amount-of-advanceable/retractable-movement detection sensor 122 (S102: Yes), it allows the amount of insertion I to be determined on the basis of the amount of advanceable/retractable movement detected by the amount-of-advanceable/retractable-movement detection sensor 122. In S103 to S109, control is implemented in accordance with the amount of insertion I that is determined on demand.

When the amount of insertion I is less than the distance X at the time of insertion of the insert part 23 (S103: Yes), the bending part 25 is not inserted through the trocar 1 as shown in FIG. 4A or, alternatively, the bending part 25 remains within the trocar 1. In this state, the bending movement of the bending part 25 is disabled (S104); that is, the driver 22 for driving the bending movement of the bending part 25 is not driven even with operation applied on the direction input part 21a.

On the other hand, when the amount of insertion I is greater than the distance X at the time of insertion of the insert part 23 (S103: No), that is, after the bending part 25 goes through the insertion path 115 through the trocar 1, the bending part 25 is positioned within the patient's abdominal space. In this state, the driver 22 is driven in accordance with operation applied on the direction input part 21a for bending movement of the bending part 25. In the embodiment described herein, it is thus possible to prevent the bending part 25 from bending within the insertion path 115 in the trocar 1 due to malfunction or the like at the time of insertion of the insert part 23 of the endoscope 2 in the abdominal space. It is also possible to effect unerring movement of the bending part 25 in the abdominal space with no need of implementing operation after estimation of the positional relation of the trocar 1 and bending part 25 that has difficulty in observation from outside.

On the other hand, withdrawal of the insert part 23 (S105: withdrawal direction) is basically much the same as insertion; however, different processing is required in the case where the amount of insertion I is within the range Y as described with reference to FIG. 3. In the state where the amount of insertion is within the range Y at the time of withdrawal, the bending part 25 is urged to go back in the insertion path 115 in the trocar 1. When the bending part 25 returns back in the insertion path 115 while it remains bent, it may possibly be damaged by the sharp edge of the insertion path 115. The bending part 25 including a moving part is often covered with a thin (protective) rubber for waterproofing and hygienic reasons. Upon withdrawal of the bending part 25 while it remains bent, this protective rubber may possibly break down. Breakage of the protective rubber will later give rise to the need for sufficient maintenance that may in turn lead to a decrease in the efficiency of the endoscope 2 during use.

In the embodiment described herein, the withdrawal of the insert part 23 is also controlled in such a way as to pass smoothly through the insertion path 115 in the trocar 1 in the same manner as described for insertion. For this reason, when the amount of insertion I is determined as being within the range Y upon movement in the withdrawal direction (S107: Yes), the bending part 25 returns back to a state where the first shaft 24a and the second shaft 24b are kept straight as depicted in FIG. 4A (S108).

Consider here that what happens when the bending part 25 goes back abruptly. It may cause the bending part 25 to come into contact the inner wall of the abdominal space by rotation of the second shaft 24b. It is then preferable to adjust the amount of the bending part 25 to go back depending on its position within the range Y, or to bend the bending part 25 after the amount of torque acting on the bending part 25 is reduced for going-back movement. Alternatively, the amount of torque acting on the bending part 25 may be just decreased. In such modes, the bending part 25 will go back such that the first shaft 24a and the second shaft 24b are kept straight in conformity with the insertion path 115 as the second shaft 24b passes through the insertion path 115.

By repeating the processing steps S103 to S108 at the time of insertion of the insert part 23, it is thus possible to carry out proper bending movement of the bending part 25. As withdrawal of the insert part 23 out of the trocar 1 is found (S109: Yes), it indicates that a sequence of processing steps gets done. In the endoscope system according to the embodiment described herein, whether the bending part 25 is to be bent or not is controlled by the direction input part 21a on the basis of the amount of insertion of the insert part 23 so that the bending part 25 can unerringly be bent in the patient's abdominal space without giving rise to any bending movement within the trocar 1. At the time of withdrawal of the insert part 23, on the other hand, the bending part 25 urged to pass through the trocar 1 is brought back or the amount of torque acting on the bending part 25 is reduced so that the endoscope 2 can be withdrawn out of the trocar 1 without any damage to the bending part 25 or while protecting it against a collision with the inner wall of the abdominal space.

Figure 10:
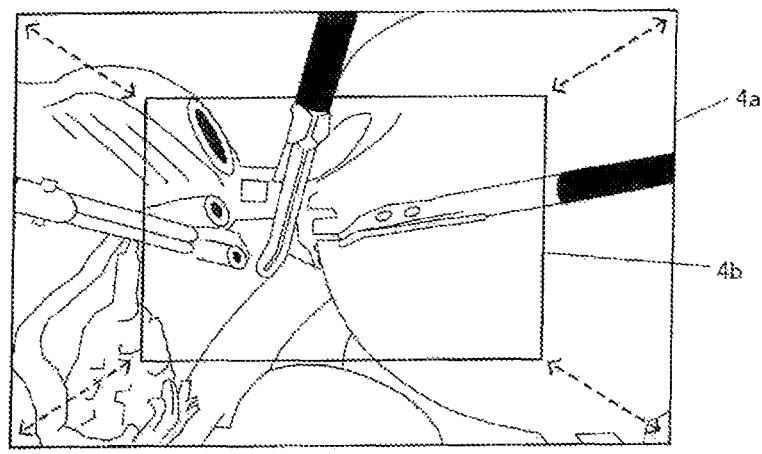
FIG. 10 is illustrative of a monitor at the time of a magnification change of the endoscope system according to one embodiment of the invention.

In the embodiment described herein, as the magnification input part 21c attached to the gripper member 26 is operated during laparoscopic surgery with the insert part 23 inserted through the abdominal space, it allows for magnification adjustment for images taken through the imaging unit 28. FIG. 10 shows an image displayed on the monitor 4 at the time of a magnification change in the endoscope system according to the embodiment described herein. Designation of magnification for the magnification input part 21c allows for zooming-in or zooming-out of taken images. FIG. 10 is illustrative of a zooming-out state 4a and a zooming-in state 4b, respectively, of images shown up on the monitor 4. With the endoscope system according to the embodiment described herein, it is thus possible to use the magnification input part 21c thereby viewing a subject of interest or an affected site in the abdominal space with an unerring magnification yet with no need for operation of the endoscope 2. Such a magnification change is of particular advantage for states where the endoscope 2 is bent at the bending part 25, because it is difficult to operate the gripper member 26 or the like to intuitively move the axis of vision of the imaging unit 28 to the desired viewing range. Note here that magnification changes may be made by means of optical zooming and/or digital zooming.

Figure 11:
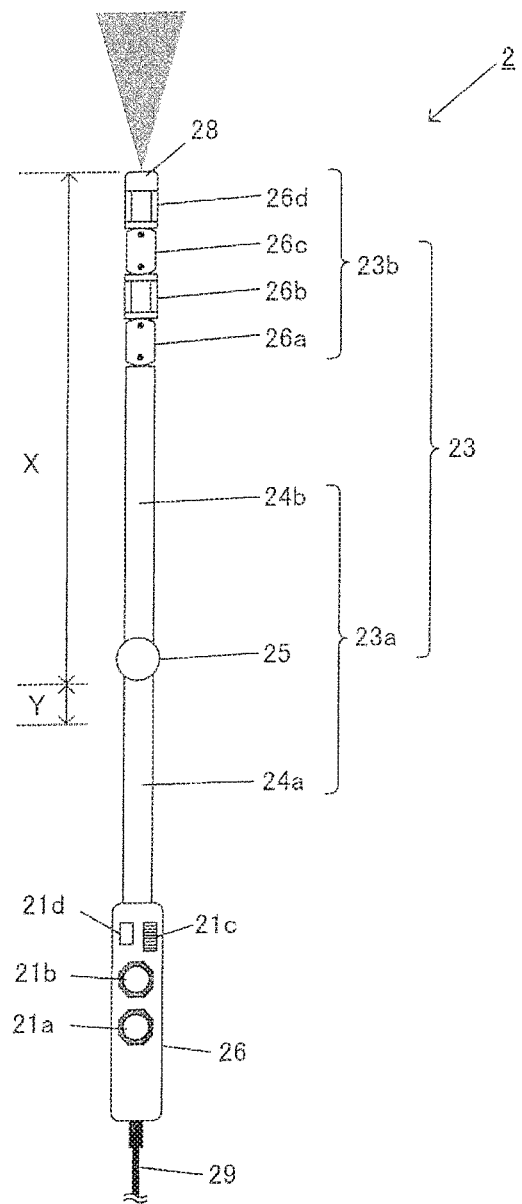
FIG. 11 is illustrative of the construction of the endoscope according to one embodiment (Example 2) of the invention.

FIG. 11 is illustrative of the construction of the endoscope 2 according to another embodiment (Example 2) of the invention. Example 1 of the endoscope 2 including the bending part 25 as a moving mechanism for the insert part 23 is different from Example 2 in that in addition to the bending part 25, there is a distal-end bending part 23b provided on the side of the imaging unit 28. This distal-end bending part 23b is different from the bending part 25 in that the latter bends across a long member (between the first shaft 24a and the second shaft 24b) while the former bends across a shorter member (between unit joints 26a to 26d). To put it another way, the bending part 25 refers to a coarse movement part capable of coarse movement whereas the distal-end bending part 23b refers to a fine movement part capable of fine movement.

Figure 12:
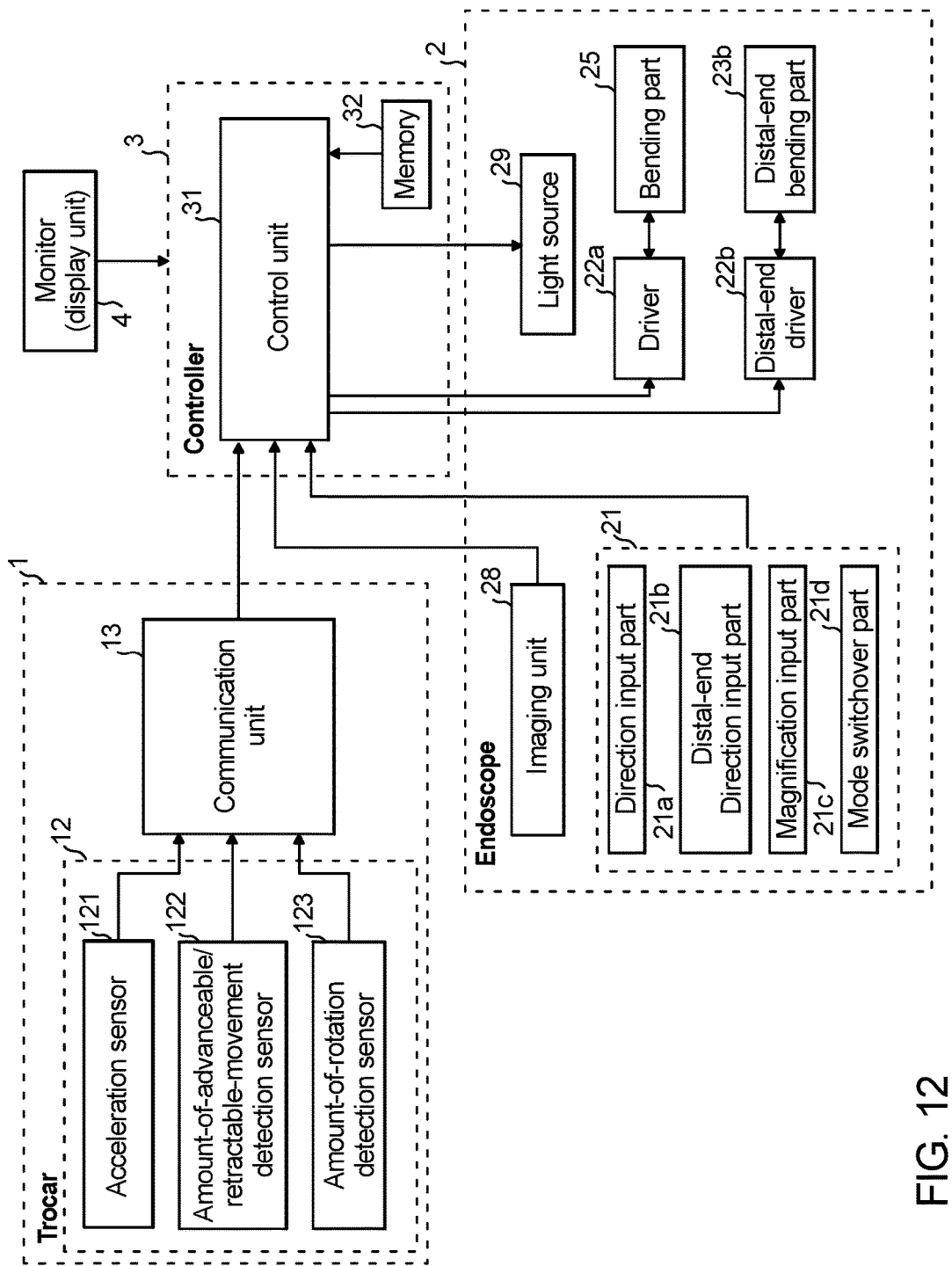
FIG. 12 is illustrative of a control configuration for the endoscope system according to one embodiment (Example 2) of the invention.

In Example 2, the gripper member 26 is provided with a distal-end direction input part 21b for designating the bending state of the distal-end bending part 23b. The gripper member 26 is further provided with a mode switchover part 21d capable of control mode selection. FIG. 12 is illustrative of a control configuration for the endoscope system according to the embodiment (Example 2) of the invention. Example 2 is different from Example 1 in that the input unit 21 includes a distal-end direction input part 21b and mode switchover part 21d, and there is a distal-end driver 22b provided for bending movement of the distal-end bending part 23b.

The bending movement of the bending part 25 takes place as in Example 1: whether the bending part 25 is to be bent or not is determined by the direction input part 21a on the basis of the amount of insertion of the insert part 23, and at the time of withdrawal, control of going-back movement or control of the amount of torque is implemented.

Figure 13:
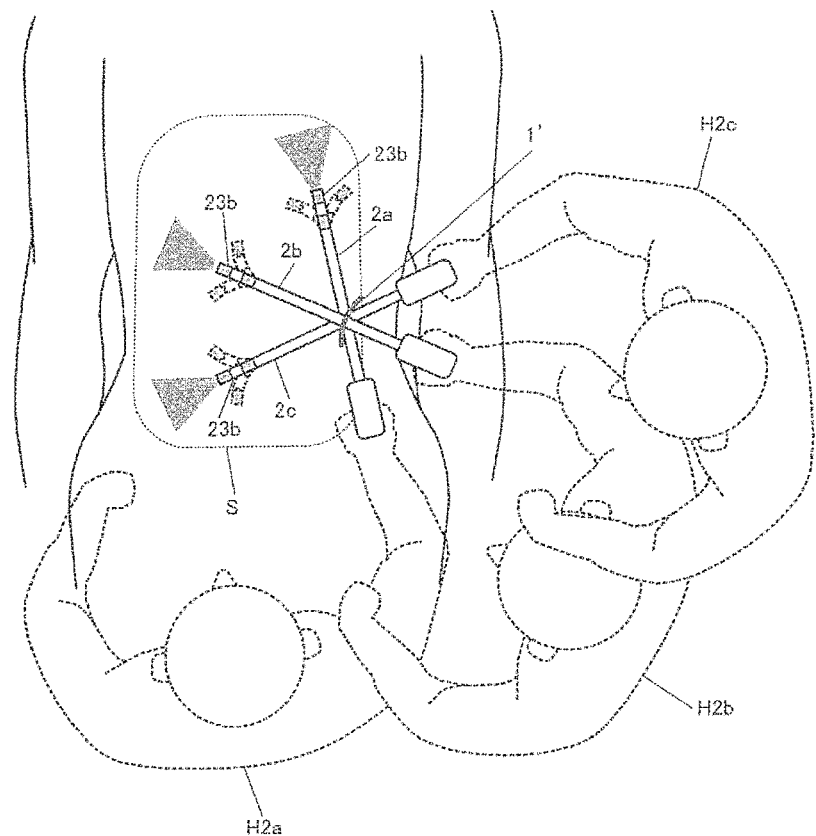
FIG. 13 is illustrative of how to carry out conventional laparoscopic surgery using an endoscope.

In Example 2, the mode switchover part 21d is operated to allow for the switchover between a normal mode and a coordinated mode. In the normal mode, the distal-end driver 22b is driven on the basis of operation of the distal-end direction input part 21b so that the distal-end bending part 23b can bend in a bending direction and an amount of bending depending on the operation or the like. FIG. 13 shows an example of operation using a conventional endoscope 2. As can also be known from the prior art endoscope 2, the incorporation of the distal-end bending part makes the imaging range of the imaging unit 28 changeable or variable. When there is the need for making a large change in the imaging range as shown in FIG. 13, however, it is required to locate the endoscope 2 as indicated by 2a, 2b and 2c. With the operability of the endoscope 2 in mind, this in turn requires for an assistant to take positions as indicated by H2a, H2b and H2c, respectively.

Figure 14:
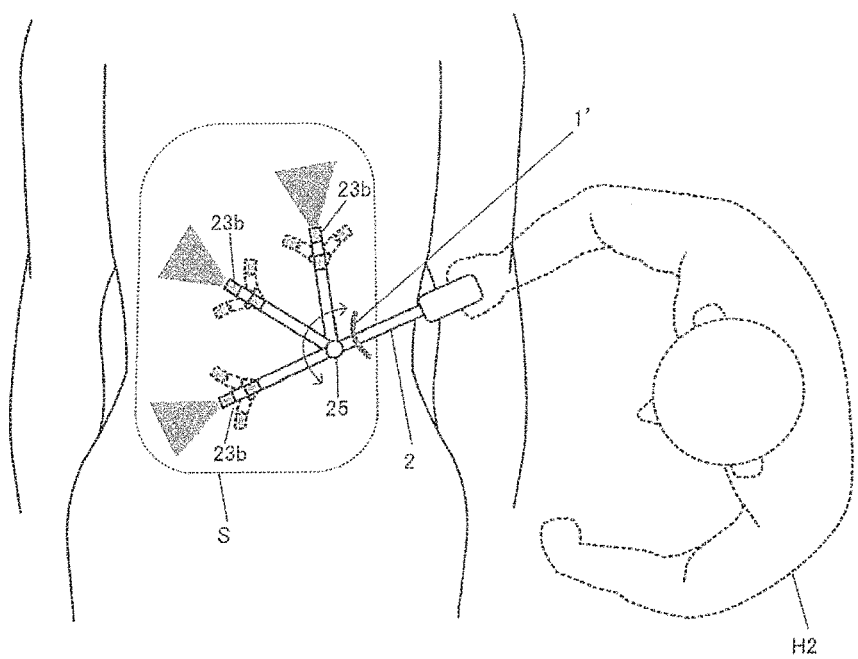
FIG. 14 is illustrative of how to carry out laparoscopic surgery using the endoscope system according to one embodiment (Example 2) of the invention.
Figure 15:
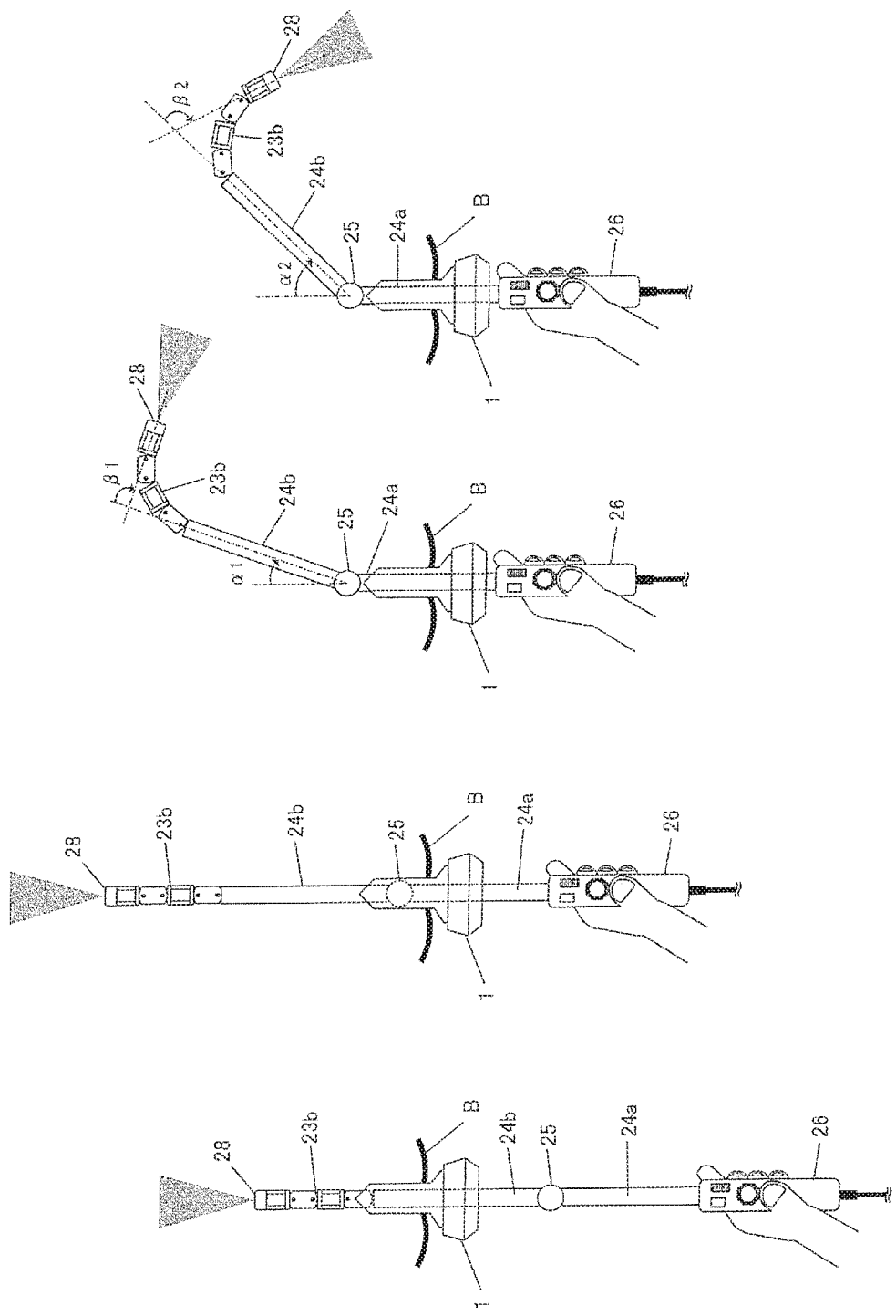
FIG. 15A-15D are illustrative of a control configuration for the endoscope according to one embodiment (Example 2) of the invention.

FIG. 14 is illustrative of how to use the endoscope 2 including the bending part 25 according to the embodiment described herein. The endoscope 2 according to this embodiment makes sure a wide imaging range by coarse movement of the bending part 25, and allows for precise imaging-position adjustment by fine movement of the distal-end bending part 23b. FIG. 15a-15D are illustrative of how the endoscope 2 of Example 2 is actuated. In such states shown in FIGS. 15(A) and 15(B), i.e., in a state where the amount of insertion I does not reach X, the bending movement of the bending part 25 by operation of the direction input part 21a is being disabled. Under a condition under which the amount of insertion I is greater than X as shown in FIGS. 15(C) and 15(D), the bending movement of the bending part 25 by operation of the direction input part 21a is enabled.

In the normal mode of the embodiment described herein, the distal-end bending part 23b bends in accordance with the operation of the distal-end direction input part 21b. The operator manipulates the distal-end direction input part 21b to direct the imaging unit 28 to the subject of interest so that the operator can find an observation position. Note here that in the embodiment described herein, it is not necessary to determine whether the distal-end bending part 23b is to be bent or not depending on the amount of insertion, because the distal-end bending part 23b is located near to the distal end of the insert part 23 so much so that the operator is able to make an easy estimation of whether or not the distal-end bending part 23b has passed through the trocar 1 enough to remain in the abdominal space. However, it is to be noted that whether the distal-end bending part 23b is to be bent or not may also be determined based on the amount of insertion like the bending part 25.

In the embodiment described herein, the operation of the mode switchover part 21d allows for the switchover from the normal mode to the coordinated mode in which the distal-end bending part 23b bends following the bending movement of the bending part 25. In the coordinated mode, input operation by the distal-end direction input part 21b may be deactivated. In the coordinated mode, for instance, the distal-end bending part 23b may bend in the same direction as the bending direction of the bending part 25.

Such movement, combined with operation of the direction input part 21a, allows the imaging unit 28 attached to the distal end of the distal-end bending part 23b to turn in the bending movement direction of the bending part 25, making it possible to check up on the movement direction of the bending part 25 with an image from the imaging unit 28. It is thus possible to check up on an obstacle or the like present in the movement direction on an image and, hence, it is possible to improve on the operability of the endoscope 2 as by moving the insert part 23 while staying away from that obstacle.

In the coordinated mode, the angle of bending α of the bending part 25 (the angle that the first shaft 24a forms with the second shaft 24b) may have some relation to the angle of bending β of the distal-end bending part 23b (the angle that the second shaft 24b forms with the imaging direction of the imaging unit 28). When the angle of bending is adjusted from α1 to α2 by operation of the direction input part 21a as shown in FIG. 15C, the angle of bending β of the distal-end bending part 23b is adjusted in association with a change in the angle of bending α of the bending part 25. In turn, this makes it possible to adjust the sensitivity (sensibility or insensibility) of an angle change in the imaging direction of the imaging unit 28 relative to a change in the angle of bending α of the bending part 25.

Figure 16:
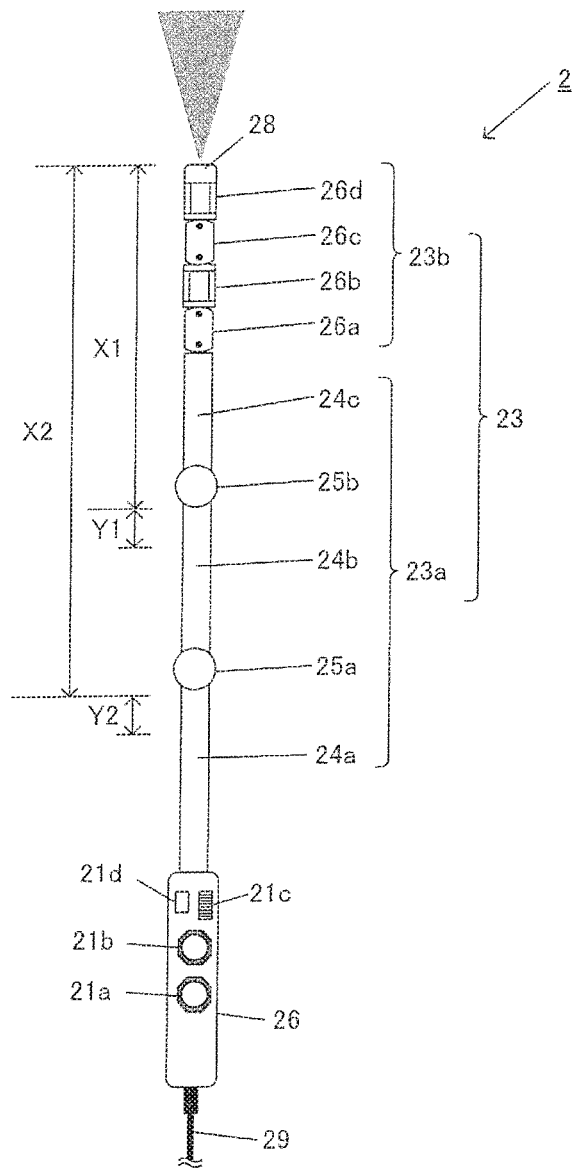
FIG. 16 is illustrative of the construction of the endoscope according to one embodiment (Example 3) of the invention.

FIG. 16 is illustrative of the construction of the endoscope 2 according to one embodiment (Example 3) of the invention. Example 3 differs from Example 2 in that there are a first bending part 25a and a second bending part 25b provided in a coarse movement part 23a. By bending the two bending parts 25a and 25b provided in the coarse movement part 23a, the number of shafts to be bent is increased from two in Example 2 to three (24a, 24b, 24c), making sure more diverse movements of the coarse movement part 23a.

While the two bending parts 25a and 25b, each rotatable with the center axis as center, are explained with reference to FIG. 16, it is to be understood that the bending parts 25a and 25b may have various forms (the same goes for the bending part 25 in Examples 1 and 2).

Figures 17A, 17B:
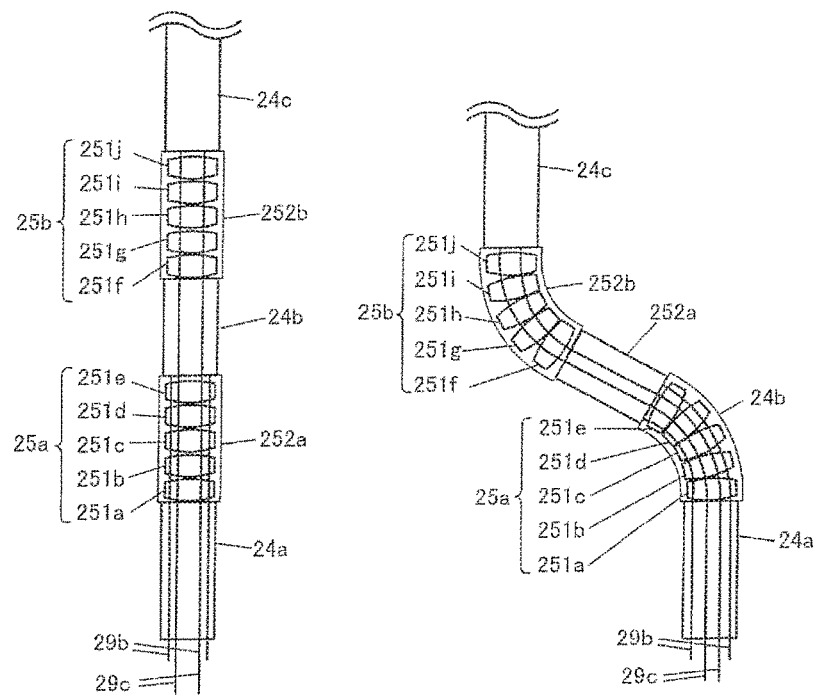
FIGS. 17A and 17B is illustrative of the construction and control configuration of the bending part according to another embodiment of the invention.

FIGS. 17A and 17B shows the construction and control configuration of a first bending part 25a and a second bending part 25b in another embodiment of the invention. In the embodiment described herein, two bending parts 25a and 25b are used as in FIG. 16; however, they are different in construction from those of FIG. 16. Here takes the first bending part 25a as an example. Within the first bending part 25a there are multiple bending pieces 251a to 251e provided. Each bending piece (251a to 251e) is shaped in such a way as to get thicker around the center and thinner with a distance from the center. The bending pieces 251a to 251e are joined together so that the first bending part 25a is bendable as shown in FIG. 17B.

Control of the rotation (bending) of the first bending part 25a may be gained by using the driver 22 to pull control wires 29b fixed to the second shaft 24b. Pulling of either one of the control wires 29b shown causes the second shaft 24b to be bent in the direction of the pulled control wire 29b. FIGS. 17A and 17B shows two control wires 29b in a plane; to achieve three-dimensional bending, however, more control wires 29b are required. The second bending part 25b is operated much in the same manner: pulling of control wires 29c allows for control of the rotation of the third shaft 24c.

In such a control configuration too, the first bending part 25a and second bending part 25b may be bent as desired to change the axis of vision of the imaging unit 28 as is the case with FIG. 16. For instance, as the first bending part 25a and second bending part 25b are rotated to place the third shaft 24c in the state of FIG. 15B, it allows for parallel movement of the distal-end bending part 23b having the imaging unit 28.

Figures 18A, 18B, 18C:
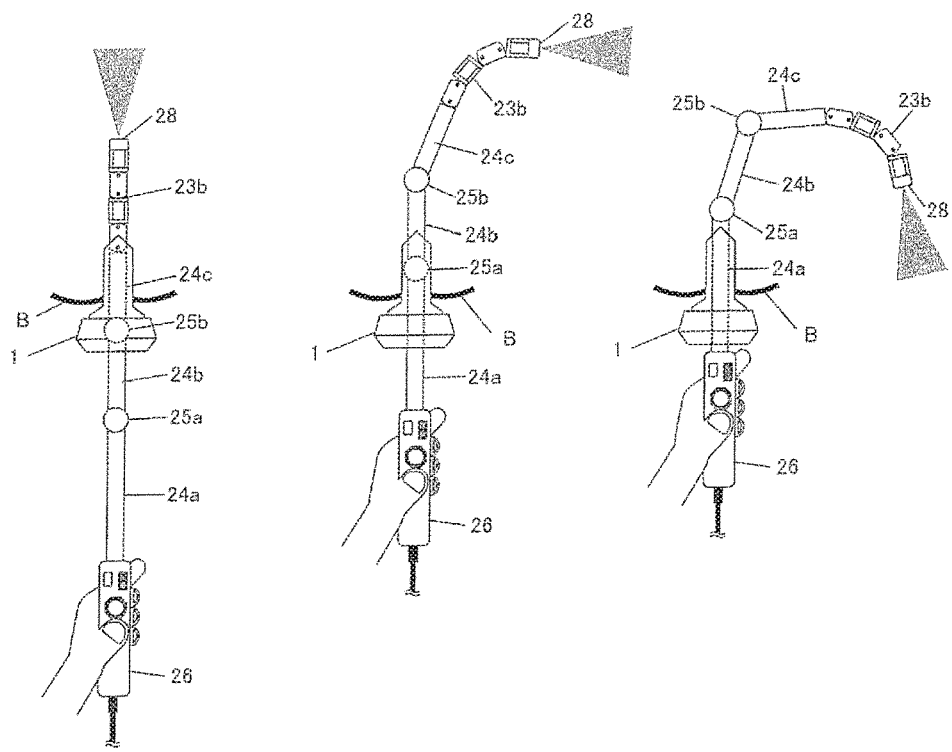
FIG. 18A-18C is illustrative of a control configuration for the endoscope system according to one embodiment (Example 3) of the invention.

FIG. 18A-18C is illustrative of a control configuration for the endoscope 2 according to the embodiment (Example 3) of the invention. In Example 3, a coarse movement part 23a is provided with a first bending part 25a and second bending part 25b to determine whether the first and second bending parts 25a and 25b are to be bent or not depending on relations between lengths X1 and X2 corresponding to the first bending part 25a and second bending part 25b and the amount of insertion; in the state of insertion of the insert part 23 shown in FIG. 18A, both the first and the second bending parts 25a and 25b are not positioned in the body cavity space and, hence, the bending movement of the first and second bending parts 25a and 25b is disabled. In the state of insertion of the insert part 23 shown in FIG. 18B, on the other hand, the second bending part 25b is positioned within the body cavity space and the first bending part 25a is positioned within the trocar 1; hence, the bending movement of the second bending part 25b alone is enabled. And in the state of insertion of the insert part 23 shown in FIG. 18C, both the first bending part 25a and second bending part 25b are positioned within the body cavity space; hence, the bending movement of the first bending part 25a and second bending part 25b is enabled.

Figure 19:
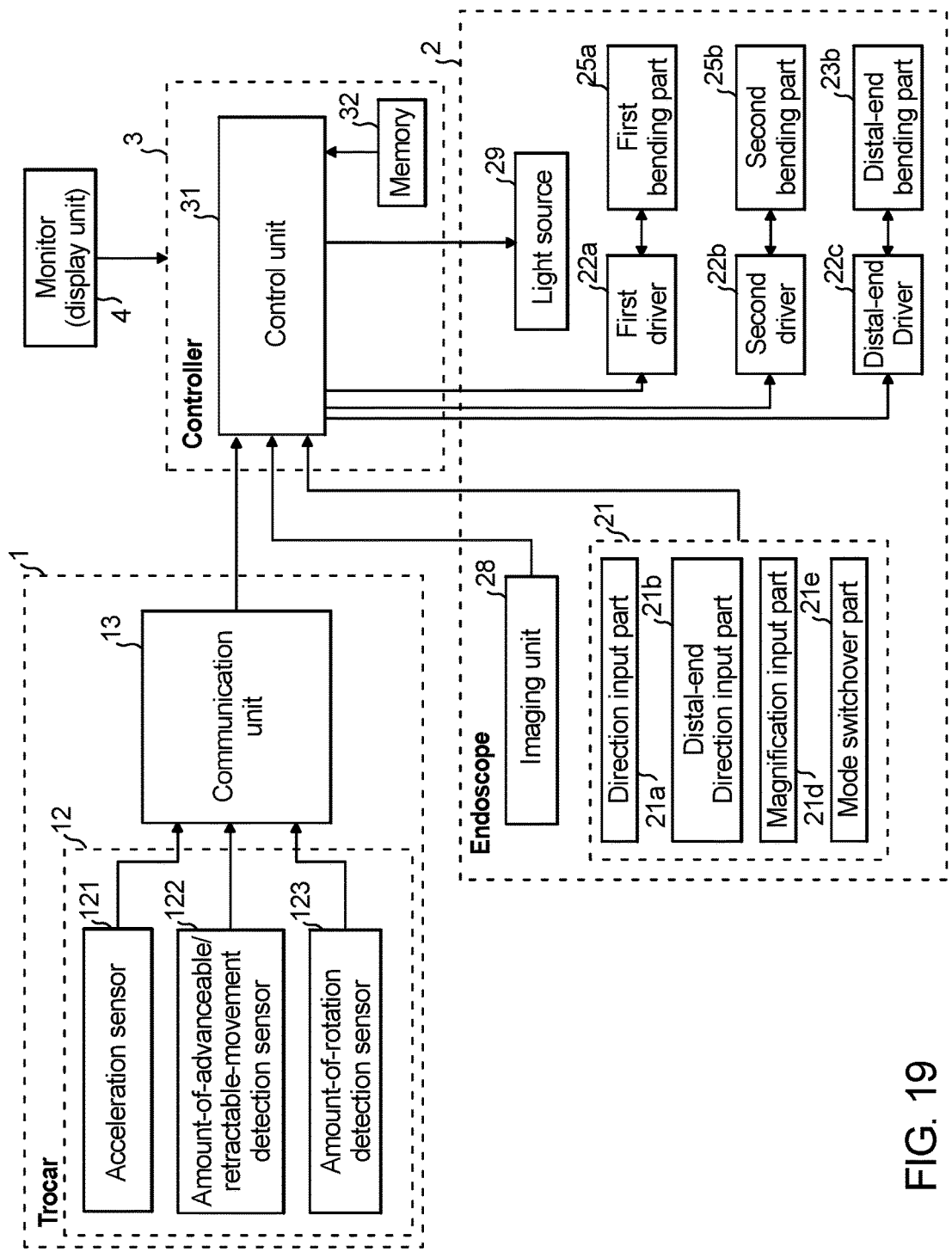
FIG. 19 is illustrative of a control configuration for the endoscope system according to one embodiment (Example 3) of the invention.

In the embodiment described herein, the coarse movement part 23a includes two bending parts (the first bending part 25a and second bending part 25b); however, it may include three or more bending parts. FIG. 19 is illustrative of the control configuration for the endoscope system according to the embodiment (Example 3) of the invention. Example 3 differs from Example 2 in that the driver used includes a first driving part 22a for bending movement of the first bending part 25a and a second driving part 22b for bending movement of the second bending part 25b. In the embodiment described herein, the first driving part 22a and the second driving part 22b are driven by only the operation of the single direction input part 21a in a cooperated manner; however, direction input parts 21a may be mounted on the first driving part 22a and the second driving part 22b, respectively.

Figure 20:
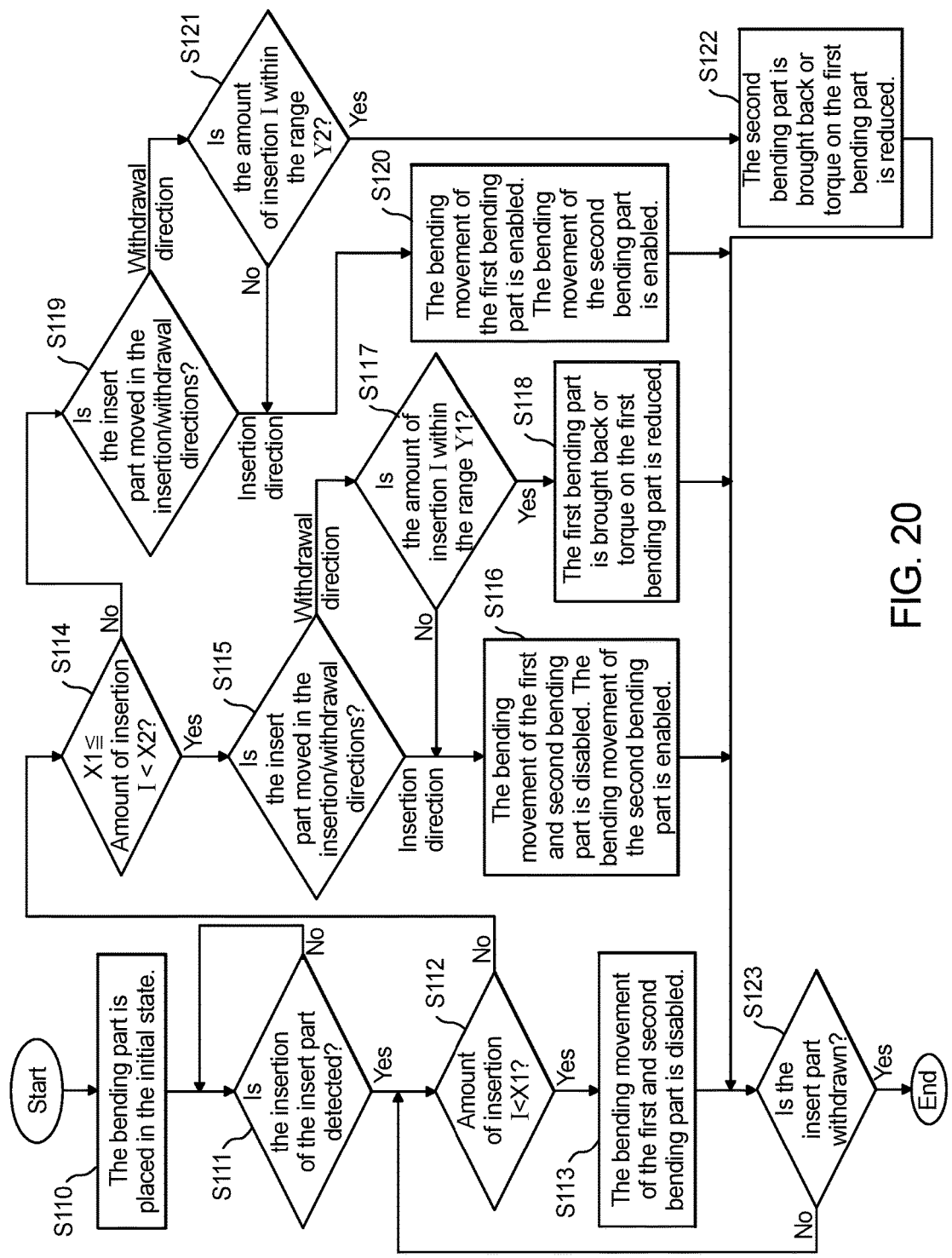
FIG. 20 is a control flow diagram for the endoscope system according to one embodiment (Example 3) of the invention.

FIG. 20 is a flowchart for control of the endoscope system according to the embodiment (Example 3) of the invention. This control is the same as control of the endoscope 2 including the single bending part 25a explained with reference to FIG. 9 with the exception that control is implemented for each bending part 25a, 25b in accordance with the amount of insertion I. First of all, the control configuration at the time of insertion (S115, S119: insertion direction) is explained. In the state of FIG. 18A, i.e., in the case where the amount of insertion I is short of length X1 (S112: Yes), the bending movement of the first bending part 25a and the second bending part 25b is disabled (S113). In the state of FIG. 18B, i.e., in the case where the amount of insertion I is greater than length X1 but not short of length X2 (S114; Yes), the bending movement of the first bending part 25a is disabled while the bending movement of the second bending part 25b is enabled (S116). And in the state of FIG. 18C, i.e., in the case where the amount of insertion I is greater than length X2 (S114: No), the bending movement of the first bending part 25a and the second bending part 25b is enabled (S120).

At the time of withdrawal of the endoscope 2 (S115, S119: withdrawal direction), on the other hand, the bending parts 25a and 25b are each brought back under a given condition and/or the torque applied on the bending parts 25a and 25b is reduced, facilitating passage of the bending parts 25a and 25b brought back through the insertion path 115 in the trocar 1 (S118, S122). Specifically, this takes place when the second bending part 25b is brought back through the insertion path 115 by withdrawal movement, i.e., the amount of insertion I is within the range Y1 shown in FIG. 16 (S117: Yes), or when the first bending part 25a is brought back through the insertion path 115, i.e., the amount of insertion I is within the range Y2 shown in FIG. 16 (S121: Yes). At the time of withdrawal, the bending parts 25a and 25b are each brought back in accordance with the amount of insertion I or the torque applied on them is reduced as mentioned above, resulting in a facility in bringing the bending parts 25a and 25b back through the insertion path 115 and prevention of the bending parts 25a and 25b from being damaged by the sharp edge of the insertion path 115.

While the embodiments according to some aspects of the invention have been described, it is to be appreciated that the invention is in no sense limited to them, and that embodiments obtainable from combinations of them are encompassed in the category of the invention too.

REFERENCE SIGNS LIST

1: Trocar
111: Upper housing
112: Lower housing
113: Cylindrical tube
14: Cable
115: Insertion path
116: Coupler member
12: Trocar sensor
121: Tilt angle detection sensor
122: Amount-of-advanceable/retractable-movement detection sensor
122a: Amount-of-advanceable/retractable-movement detection roller
122b: Photosensor
123: Amount-of-rotation detection sensor
123a: Amount-of-rotation detection roller
123b: Photosensor
13: Communication unit
2: Medical instrument (endoscope)
2': Medical instrument (forceps)
21: Input unit
21a: Direction input part
21b: Distal-end direction input part,
21c: Magnification input part
21d: Mode switchover part
22: Driver
22a: First driving part
22b: Second driving part
22c: Distal-end driver
23: Insert part
23a: Coarse movement part
23b: Distal-end bending part (fine movement part)
24a: First shaft
24b: Second shaft
24c: Third shaft
25: Bending part
25a: First bending part
25b: Second bending part
26a to 26d: Unit joints
251a to 251j: Bending pieces
28: Imaging unit
29: Light source
3: Controller
31: Control unit
32: Memory
4: Monitor (Display unit)

The invention claimed is:

1. An endoscope system comprising:
an insert part configured to be inserted into a body, the insert part comprising:
an imaging unit;
a first bending part provided proximally relative to the imaging unit; and
a second bending part provided proximally relative to the first bending part;
an actuator configured to bend the first bending part and to bend the second bending part;
an input unit configured to operate the first bending part and to operate the second bending part by an operator;
a trocar configured for insertion of a shaft assembly, the shaft assembly comprising the imaging unit, the first bending part and the second bending part;
a movement sensor provided at the trocar, the movement sensor being configured to detect a quantity of insertion or withdrawal of the shaft assembly; and
a controller configured to control the actuator based on an input signal from the input unit;
wherein the input unit further comprises a mode switch unit configured to switch between a normal mode and a cooperative mode;
the controller comprising one or more processors, the controller being configured to:
receive an amount of insertion or withdrawal of the insert part from the movement sensor;
receive the input signal from the input unit; and
generate a drive command of the actuator based on the amount of insertion of the shaft assembly and the input signal, wherein in response to switching to the cooperative mode, the drive command is configured to cooperatively actuate at least one of the first bending part and the second bending part so as to keep a cooperative relationship between the first bending part and the second bending part, the cooperative relationship being a drive command configured to control an angle of bending of the first bending part on the basis of a bending angle of the second bending part; and
send the drive command to the actuator.

2. The endoscope system according to claim 1, wherein the controller is further configured to determine whether a current operation is configured to insert or withdraw the shaft assembly on the basis of a change in the amount of insertion, wherein when the current operation is configured for withdrawal of the shaft assembly, the controller generates a command of the actuator and sends the command to the actuator such that, on the basis of the received amount of insertion, the first bending part and the second bending part return to an initial state with no bending of the first bending part or no bending of the second bending part, or alternatively an amount of torque of the actuator on the first bending part or on the second bending part decreases.

3. The endoscope system according to claim 1, wherein:
the input unit comprises a mode switch part, a distal-end direction input part configured to operate the first bending part, and a direction input part configured to operate the second bending part, and
the controller is configured to:
in response to switching to the normal mode, receive signals from the distal-end direction input part and the direction input part, generate commands for actuation of the first bending part and the second bending part based on the commands from the distal-end direction input part and the direction input part, and send the commands to the actuator.

4. The endoscope system according to claim 3, wherein the controller is configured to:
   in response to switching the cooperative mode, disable a command from the distal-end direction input part.

* * * * *